(12) United States Patent
Chen et al.

(10) Patent No.: US 10,336,944 B2
(45) Date of Patent: Jul. 2, 2019

(54) DIRECT SYNTHESIS OF HYDROCARBONS FROM CO-ELECTROLYSIS SOLID OXIDE CELL

(71) Applicant: University of South Carolina, Columbia, SC (US)

(72) Inventors: Fanglin Chen, Irmo, SC (US); Libin Lei, Columbia, SC (US); Tong Liu, Columbia, SC (US); Shumin Fang, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 15/711,634

(22) Filed: Sep. 21, 2017

(65) Prior Publication Data

US 2018/0086984 A1 Mar. 29, 2018

Related U.S. Application Data

(60) Provisional application No. 62/400,244, filed on Sep. 27, 2016.

(51) Int. Cl.
| | | |
|---|---|---|
| *C25B 1/04* | (2006.01) | |
| *C25B 9/00* | (2006.01) | |
| *C25B 9/08* | (2006.01) | |
| *C25B 9/06* | (2006.01) | |
| *C10G 2/00* | (2006.01) | |
| *C25B 3/04* | (2006.01) | |
| *B01J 23/10* | (2006.01) | |
| *B01J 23/78* | (2006.01) | |
| *C25B 15/02* | (2006.01) | |
| *C25B 15/08* | (2006.01) | |
| *C25B 9/10* | (2006.01) | |

(Continued)

(52) U.S. Cl.
CPC ............ *C10G 2/35* (2013.01); *B01J 23/10* (2013.01); *B01J 23/78* (2013.01); *C10G 2/332* (2013.01); *C10G 2/34* (2013.01); *C10G 2/40* (2013.01); *C10G 2/50* (2013.01); *C25B 3/04* (2013.01); *C25B 9/10* (2013.01); *C25B 15/02* (2013.01); *C25B 15/08* (2013.01); *C07C 1/10* (2013.01); *C07C 1/12* (2013.01)

(58) Field of Classification Search
CPC .......... C25B 15/02; C25B 15/08; C25B 1/04; C25B 9/00; C25B 9/06; C25B 9/08; Y02E 60/366
USPC ........................................... 204/241
See application file for complete search history.

(56) References Cited

U.S. PATENT DOCUMENTS

| | | |
|---|---|---|
| 8,394,352 B2 | 3/2013 | Chen et al. |
| 8,465,797 B2 | 6/2013 | Chen et al. |
| 8,778,560 B2 | 7/2014 | Chen et al. |

(Continued)

*Primary Examiner* — Zulmariam Mendez
(74) *Attorney, Agent, or Firm* — Dority & Manning, PA (57) ABSTRACT

A hydrocarbon generation system that combines a solid oxide electrolysis cell (SOEC) and a Fischer-Tropsch unit in a single microtubular reactor is described. This system can directly synthesize hydrocarbons from carbon dioxide and water. High temperature co-electrolysis of $H_2O$ and $CO_2$ and low temperature Fischer-Tropsch (F-T) process are integrated in a single microtubular reactor by designation of a temperature gradient along the axial length of the microtubular reactor. The microtubular reactor can provide direct conversion of $CO_2$ to hydrocarbons for use as feedstock or energy storage.

11 Claims, 3 Drawing Sheets

(51) Int. Cl.
  *C07C 1/12* (2006.01)
  *C07C 1/10* (2006.01)

(56) References Cited

U.S. PATENT DOCUMENTS

| | | |
|---|---|---|
| 8,818,056 B2 | 8/2014 | Chen et al. |
| 8,835,003 B2 | 9/2014 | Chen et al. |
| 9,153,831 B2 | 10/2015 | Chen et al. |
| 9,240,597 B2 | 1/2016 | Chen et al. |
| 9,406,944 B2 | 8/2016 | Chen et al. |
| 9,574,274 B2 | 2/2017 | Chen et al. |
| 9,687,775 B2 | 6/2017 | Chen et al. |
| 9,825,306 B2 | 11/2017 | Chen et al. |
| 2008/0283411 A1* | 11/2008 | Eastman .............. C10G 2/30 205/343 |
| 2013/0164536 A1 | 6/2013 | Chen et al. |
| 2014/0287345 A1 | 9/2014 | Chen et al. |
| 2015/0299871 A1 | 10/2015 | Chen et al. |
| 2015/0314232 A1 | 11/2015 | Chen et al. |
| 2017/0292197 A1 | 10/2017 | Lei et al. |

* cited by examiner

DIRECT SYNTHESIS OF HYDROCARBONS FROM CO-ELECTROLYSIS SOLID OXIDE CELL

CROSS REFERENCE TO RELATED APPLICATION

This application claims filing benefit of U.S. Provisional Patent Application Ser. No. 62/400,244 having a filing date of Sep. 27, 2016, which is incorporated herein by reference for all purposes.

FEDERAL RESEARCH STATEMENT

This invention was made with Government support under Grant No. DMR-1210792, awarded by U.S. national Science Foundation. The Government has certain rights in the invention.

BACKGROUND

Fossil fuels, such as coal, oil, and natural gas are non-renewable energy sources and their ever-increasing consumption leads to excessive emission of greenhouse gases, and in particular carbon dioxide ($CO_2$). To mitigate negative consequences of fossil fuel use, methods for reduction of carbon emission have been implemented, but with marginal success. Concern over fossil fuel use has also led to global development and implementation of renewable energy sources over the past decades. Renewable energy sources such as biomass are increasingly harvested to generate energy and raw materials (e.g., via gasification), but substantial technical issues remain due to low quality products and excess ash formation.

Co-electrolysis of steam and carbon dioxide by use of solid oxide electrolysis cells (SOECs) is a promising method that can efficiently transform carbon dioxide and water into syngas (a mixture of $H_2$ and CO), which can subsequently be used as feedstock for chemical synthesis, for instance through the well-established Fischer-Tropsch (F-T) process to produce liquid hydrocarbons. Liquid hydrocarbons are often preferred to syngas as feedstock materials as they can be more easily and more safely stored and transported using existing infrastructure.

Unfortunately, there are still major challenges for large scale deployment of SOECs in hydrocarbon generation. One principal challenge is that syngas production via co-electrolysis is a high temperature process (normally from about 600° C. to about 1000° C.) and integration of this high temperature process with lower temperature syngas processing techniques such as F-T processing (normally from about 200° C. to about 500° C.) presents significant technical challenges.

What are needed in the art are methods and systems that can successfully integrate solid oxide cell co-electrolysis processes with syngas utilization processes to improve use of renewable energy sources and decrease carbon emissions. Such integration can not only provide scalable energy storage, but can also be utilized to produce chemicals or fuel by use of recycled $CO_2$.

SUMMARY

According to one embodiment, disclosed is a hydrocarbon generation system that includes a microtubular reactor. The microtubular reactor includes a first region designed for syngas generation and a second region downstream of the first region that is designed for hydrocarbon generation. More specifically, the first region includes a cathode and an anode in electrical communication with one another and an oxygen ion conducting electrolyte between the cathode and an anode so as to form a solid oxide electrolysis cell (SOEC). The second region includes a Fischer-Tropsch reaction catalyst that is in fluid communication with the cathode of the first region. The system also includes a temperature control unit that is configured to heat the first region to a first temperature that is greater than a second temperature of the second region.

Also disclosed is a method for generating hydrocarbons by use of the systems. In general, a method can include heating the first region of a microtubular reactor to a first temperature and flowing a feed stream to the first region; the feed stream including steam and/or water and also including carbon dioxide. The method also includes collecting a product hydrocarbon downstream of the second region of the microtubular reactor, the second region being downstream of the first region and operating at a second temperature that is less than the first temperature. According to the method, the product hydrocarbon can be formed in the second region according to a Fischer-Tropsch reaction that utilizes a syngas generated in the first region according to a co-electrolysis process.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

The following description and other modifications and variations to the present invention may be practiced by those of ordinary skill in the art, without departing from the spirit and scope of the present invention. In addition, it should be understood that aspects of the various embodiments may be interchanged both in whole and in part. Furthermore, those of ordinary skill in the art will appreciate that the following description is by way of example only, and is not intended to limit the invention.

The present disclosure is generally directed to a hydrocarbon generation system that combines a solid oxide electrolysis cell (SOEC) and a Fischer-Tropsch (F-T) reactor as separate regions in a single microtubular reactor. This system can be beneficially utilized for direct synthesis of hydrocarbons from carbon dioxide and water. More specifically, high temperature co-electrolysis of $H_2O$ and $CO_2$ and low temperature Fischer-Tropsch (F-T) processes are integrated in the reactor by designation of a temperature gradient along the axial length of the microtubular reactor so as to provide favorable temperature conditions for both processes. The small size of the tubular reactor, having an outer diameter of about 3 millimeters or less, for instance between about 1 and about 3 mm in some embodiments, can provide high thermal shock resistance, large electrode surface area and high current density per unit volume for the electrolysis region of the reactor, and can also provide large catalyst surface area per unit volume for the F-T region, resulting in high $CO_2$ conversion rate and high yield of hydrocarbons. The microtubular reactors can provide for direct conversion of $CO_2$ to hydrocarbons ($C_1$-$C_n$) for use as feedstock or energy storage.

Disclosed systems can, among other benefits, provide a potential pathway for efficient and eco-friendly utilization of carbon (e.g., coal, biomass, etc.) and $CO_2$ to produce clean hydrocarbons, and in one embodiment can provide a carbon neutral sustainable hydrocarbon supply. Beneficially, the liquid synthetic hydrocarbon products formed by use of the system can more easily be stored and transported using existing infrastructure as compared with syngas of a gasification or stand-alone electrolysis process. Moreover, the hydrocarbon production method does not require pure $CO_2$, which is more flexible for practical adoption.

Figure 1:
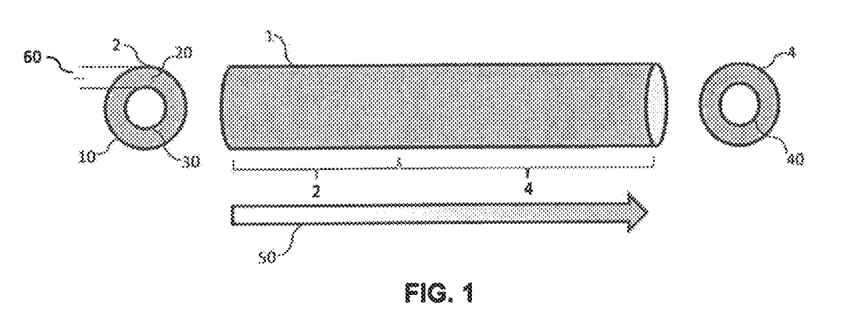
FIG. 1 provides a schematic illustration of one embodiment of a microtubular reactor as may be utilized for direct synthesis of hydrocarbons as described.

A schematic of a representative microtubular reactor 1 is illustrated in FIG. 1 in a side view. The reactor 1 includes a first region 2 and a second region 4 that extend along axial lengths of the reactor 1. To the left of the side view of the reactor 1 is illustrated a cross-sectional view of the first region 2 and to the right of the side view of the reactor 1 is a cross sectional view of the second region 4.

The first region 2 of the reactor 1 is configured to operate as an SOEC. The SOEC of the first region 2 of the reactor 1 includes three primary components including two electrodes 10, 30 (i.e., an anode 10 and a cathode 30) and an electrolyte 20 between and separating the anode 10 and the cathode 30. While the illustrated embodiment includes the anode 10 on the outer surface of the reactor wall and the cathode 30 on the inner surface of the reactor wall, this is not a requirement of the disclosed systems, and the cathode can alternatively be located on the outer surface of a microtubular reactor.

A microtubular SOEC can be formed according to any suitable methodology and by use of standard materials as are generally known in the art. By way of example, in one embodiment, a microtubular SOEC can be formed according to the methods as disclosed in U.S. Pat. No. 8,465,797 to Chen, et al., which is incorporated herein by reference for all purposes. Briefly, this formation method can include spinning a ceramic solution to form a tubular precursor. To form a porous layer of the SOEC (e.g., a cathode or anode layer), the precursor can be immersed in water to encourage a phase inversion in which water molecules and spinning solution molecules exchange resulting in a porous ceramic green structure. The porous ceramic structure can then be washed, dried, and fired. Following, one or more additional layers of the same or a different ceramic can be coated on to either the inner or outer surface of the precursor structure, dried, and fired to form additional layers of the SOEC. The existence and size of porosity of each layer can be controlled through control of the processing parameters such as viscosity of the ceramic slurry and the like. For instance, to form a dense electrolyte layer, the formation process does not need to include a phase inversion step prior to firing of the ceramic.

Of course, the formation method utilized to form the microtubular SOEC is not limited to a phase inversion/co-sintering method as described above, and the microtubular SOEC can be formed from desired electrode and electrolyte materials in powder form according to any known process. For instance, the powders can generally be compacted by various known techniques such as pressing, extrusion, slip casting, and others, and can then be sintered into porous shapes, according to standard practice.

The materials used to form the layers of the microtubular SOEC can include cathode, electrolyte, and anode materials as are generally known in the art. For instance, the cathode of the microtubular SOEC may include materials conventionally used with SOECs. In general, the cathode may be porous so as to improve contact between the cathode materials and the reactants, as is known. For example, a cathode can include a nickel-zirconia cermet material including ceramics such as, and without limitation, nickel-yttria stabilized zirconia (Ni—YSZ), nickel-samaria doped ceria (Ni-SDC), nickel-gadolinium doped ceria (Ni-GDC) as well as combinations thereof as are known in the art. Cathode materials can include, by way of example and without limitation, Ni—YSZ, Ni—ScSZ, Ni-LSGM, Ni-SDC/GDC, etc. Other cathode materials such as electronic conducting perovskites may be utilized including, without limitation, $LaMO_x$ type (e.g. $La_2NiO_4$), where M is typically a transition metal, perovskite-type lanthanum chromite ($LaCrO_3$), lanthanum strontium manganese chromate (LSCM), $Sr_2Fe_{2-x-y}Mo_xM_yO_{6-\delta}$ in which M is a transition metal element (e.g., $Sr_2Fe_{1.5}Mo_{0.5}O_{6-\delta}$ (SFM)) and scandium-doped LSCM (LSCMS) are also encompassed. In one embodiment, the cathode material can include a perovskite material having the general formula of $La_{1-x}M1_xM2O_{3-\delta}$ in which M1 is an alkaline earth element and M2 is a transition metal element. However, it should be understood that the materials used to form a cathode may include any material as is known in the art for use in an SOEC cathode.

Suitable anode materials can include, by way of example and without limitation, a solid electrode phase such as lanthanum strontium cobalt iron oxide (LSCF), LSM, LSM impregnated with gadolinium doped ceria (GDC), $Sr_2Fe_{1.5}Mo_{0.5}O_{6-\delta}$ SFM), $La_{0.7}Ca_{0.3}Cr_{0.97}O_3$ (LCC), strontium-doped lanthanum manganite, strontium-doped lanthanum manganite impregnated with ceria-based catalyst, $Sr_2Fe_{2-x-y}Mo_xM_yO_{6-\delta}$ in which M is a transition metal element, $La_{1-x}M1_xM2O_{3-\delta}$ in which M1 is an alkaline earth element and M2 is a transition metal element, or combinations thereof.

The electrolyte may be formed of any oxygen-ion conducting electrolyte material as is known in the art. For example, the oxygen-ion conducting electrolyte may include, but is not limited to, yttria stabilized zirconia (YSZ), scandia stabilized zirconia (SSZ), lanthanum gallate-based oxide materials (LSGM) (e.g., $(La_{0.6}Sr_{0.4})(Ga_{0.8}Mg_{0.2})O_3$), scandium stabilized zirconia (ScSZ), doped ceria ($CeO_2$), as well as combinations of electrolyte materials.

Electricity can be provided to the SOEC by any suitable power source 60 to provide a voltage potential across the electrodes of the SOEC, as shown. For example, a power source may include any direct current power source such as may be provided from a commercial power grid; a generator powered by gas, electricity, wind, water, steam, nuclear energy, solar energy, or other energy source; a battery or battery array; or any other conventional power source capable of supplying an electrical current to the SOEC.

Referring again to FIG. 1, downstream of the first region 2, the microtubular reactor 1 can include a second region 4.

The second region can include an F-T reactor region that is in communication with and downstream of the cathode of the SOEC.

To form the F-T reaction region, an F-T catalyst can be deposited on a surface of the microtubular reactor that is in the second region 4 and downstream of the cathode of the SOEC of the first region. For instance, in the illustrated embodiment, in which the cathode 30 is on the inner surface of the SOEC of the first region 2, the second region 4 can include an F-T catalyst 40 that is on the inner surface of the second region 4, as shown. Thus, following formation of syngas at the cathode in the first region 2 of the microtubular reactor 1, the syngas can flow to the second region 4 where it can contact the catalyst 40 and generate hydrocarbons according to an F-T reaction.

The F-T catalyst can include any F-T catalyst or combination thereof as is known in the art including, without limitation transition metals such as cobalt, iron, nickel, nickeliplatinum alloy, rhodium, ruthenium, palladium, osmium, vanadium, iron, manganese, etc., as well as combinations of catalysts.

The F-T catalyst can be located on the surface of a previously formed microtubular SOEC to form the F-T region of a microtubular reactor. The method utilized to locate the catalyst on the surface can vary, with preferred methods generally depending upon the surface upon which the catalyst will be located (i.e., the inner surface or the outer surface of the tube) as well as the nature of that surface. For instance, in the illustrated embodiment of FIG. 1, in which the F-T catalyst is located on the inner surface of the microtubular reactor, the second region 4 can be dip-coated with a solution including the catalyst followed by drying of the solution to form a coating including the F-T catalyst in the second region 4. Of course, other application methods can alternatively be utilized such as brush coating, atomic layer deposition, and the like. Non-contact deposition methods such as atomic layer deposition may be of benefit in those embodiments in which the F-T catalyst is located on an inner surface of the microtubular reactor.

The second region 4 can include additional materials in conjunction with the F-T catalyst (e.g., on the surface of the tubular reactor) as are known in the art to further encourage the F-T reactions. For instance support materials such as metal oxides, tungsten carbides, and the like may be utilized in conjunction with the F-T catalysts, which can affect the activity of the catalysts as is known and provide hydrocarbon products with particularly desired characteristics.

In addition to the first and second regions 2, 4, the system can include a temperature control unit 25 in conjunction with the microtubular reactor 1. Any suitable direct or indirect temperature control system can be utilized that can provide a suitable SOEC reaction temperature in the first region 2 of the reactor 1 and a temperature gradient 50 extending along the length of the microtubular reactor. In particular, the first region 2 can be heated to a higher temperature than the second region 4 in order to provide a lower temperature in the second region 4 and encourage the F-T reaction. As such, the temperature control unit 25 can include one, two, or more temperature sensors 26 in communication with the reactor 1 and the temperature control unit 25.

The existence of temperature gradient 50 along the microtubular reactor 1 can provide suitable temperature conditions for both processes. Accordingly, in the first region 2, a temperature of from about 600° C. to about 1000° C. can be attained so as to encourage the electrolysis process and produce a syngas through the supply of external electricity from the power source 60.

The syngas can then flow directly to the second region 4 in which the F-T process can take place, generally at a reaction temperature of from about 200° C. to about 500° C. Within the second region, the $H_2$ and CO of the syngas can react to form hydrocarbons. Thus along the length of the microtubular reactor 1, there can be temperature zones for the two processes, achieving the integration of the higher temperature electrolysis process and the lower temperature F-T process in a single device.

According to a process, a feed stream can be provided to the microtubular reactor 1. The feed stream can include water, generally in the form of steam ($H_2O$) and carbon dioxide ($CO_2$) and can be introduced to the first region 2 of the reactor 1, and specifically to the cathode side of the SOEC, where steam ($H_2O$) and carbon dioxide ($CO_2$) receive electrons from an external power source 60 to produce hydrogen gas ($H_2$), carbon monoxide (CO) and oxygen ions ($O^{2-}$), described in reactions (1) and (2) below. On the cathode side of the SOEC, $CO_2$ and $H_2O$ fed to the cell are electrochemically converted to syngas, similar to co-electrolysis conversion processes as are known in conventional electrolysis systems. A reverse water gas shift reaction can also take place at the cathode side, as described in reaction (3) in which carbon dioxide introduced to the cathode can react with hydrogen produced in reaction (1). In one embodiment, additional hydrogen gas ($H_2$) can also be provided in the feed stream to push the reverse water gas shift reaction to the CO production side and form additional CO for hydrocarbon generation downstream. Optionally, however, reaction (3) can be carried out with only the hydrogen produced in reaction (1).

$$H_2O + 2e^- \rightarrow H_2 + O^{2-} \tag{1}$$

$$CO_2 + 2e^- \rightarrow CO + O^{2-} \tag{2}$$

$$CO_2 + H_2 \rightarrow CO + H_2O \tag{3}$$

The oxygen ions ($O^{2-}$) produced at the cathode can be transported through the electrolyte to the anode side by the effect of concentration diffusion and/or by assistance of an external applied electrical field.

On the anode side, the oxygen ions can be oxidized to form oxygen, illustrated as reaction (4):

$$2O^{2-} \rightarrow O_2 + 4e^- \tag{4}$$

Thus the total reaction of the solid oxide co-electrolysis process is shown as reaction (5):

$$H_2O(g) + CO_2(g) \rightarrow H_2(g) + CO(g) + O_2(g) \tag{5}$$

FIG. 1 illustrates a system as described herein that includes an F-T reactor unit 4 in fluid communication and downstream of the SOEC 2.

The carbon dioxide of the feed can be obtained from any suitable source. For example, carbon dioxide stored in a gas or liquid state may be included as a component of a feed stream to the microtubular reactor. Carbon dioxide produced as an off-gas or waste gas in a manufacturing process can be used as a source of carbon dioxide. In some embodiments, carbon dioxide from the combustion of coal, gas, oil, wastes, or other materials, from petrochemical refining processes, or from biological reduction processes may provide a source for the $CO_2$ feed. In one embodiment, a power plant, e.g., a coal-fired, gas-fired or any other type of power plant including, without limitation, oil-fired, biofuel, or nuclear power plant may serve as a source of a carbon dioxide feed to the hydrocarbon generation system.

A carbon dioxide source may additionally provide energy for use in the hydrocarbon production process, e.g., electrical energy or heat. For example, waste heat produced at a power plant may be used to heat the carbon dioxide stream(s), the microtubular reactor, and/or to form steam of a feed stream. Similarly, electricity produced by a power plant may be used in a hydrocarbon production process to provide the necessary voltage potential to the SOEC and/or to heat the microtubular reactor. Electricity produced by a power plant may also be used to generate steam or other necessary components for a hydrocarbon production process.

It can be beneficial in some embodiments to provide the $H_2O$ and $CO_2$ to the SOEC at an increased temperature, such as about 500° C. or higher, for instance at temperatures from about 500° C. (773 K) to about 1000° C. (1273 K) in some embodiments. When heated, feed stream may be heated using conventional techniques. For example, a feed stream can be fed to the SOEC by a suitable pipe that can be wrapped with electrical heat tape, that can be exposed to steam such as by use of a conventional heat exchanger, or by any other system.

The feed to the cathode side of the first region 2 can be controlled so as to produce a syngas with a desired ratio of product components. For instance, the ratio of the $CO_2$ to $H_2O$ and the optional inclusion of $H_2$ in the feed to the cathode can be controlled to control the $H_2$:CO ratio of the syngas. In one embodiment, the $CO_2$:$H_2O$:$H_2$ ratio can be controlled to prove the syngas off of the cathode with a $H_2$:CO ratio of from about 1:1 to about 3:1, or about 2:1 in some embodiments.

The electrolysis reactions carried out at the cathode side of the SOEC can generally be carried out at temperatures from about 500° C. to about 1200° C., or from about 800° C. to about 1000° C. in some embodiments. As such the syngas formed at the cathode side of the SOEC can be at or above about 500° C. in some embodiments. By development of the temperature gradient 50 along the length of the microtubular reactor 1, this syngas product can be cooled (either actively or passively) in order that it is at a suitable temperature at the F-T reaction region.

The syngas ($H_2$—CO) generated in the electrolysis process in the first region 2 flows along the microtubular reactor 1 and arrives in the second region 4 where the F-T catalyst is located and the F-T process can take place. In conjunction with the catalyst, $H_2$ and CO of the syngas can react to produce hydrocarbons, as shown in reaction (6):

$$xCO + (0.5y+x)H_2 \rightarrow C_xH_y + xH_2O \tag{6}$$

Compared with conventional tubular reactor (plug flow reactor), a microtubular reactor as described herein with a small tube diameter can provide greater thermal shock resistance, larger electrode area per unit volume for electrolysis and larger catalyst surface area per unit volume for F-T reaction. For instance, for a tubular unit, the volume of reactant gas inside the tube can be calculated by equation (7):

$$V_{reactant} = \frac{1}{4}\pi d^2 l \tag{7}$$

in which:
d is the inner diameter of tube,
l is the length of tube.

The catalyst surface area in the tube is proportional to the inner surface area of a tube and can be calculated by equation (8):

$$S_{cata} = \pi dlC \tag{8}$$

in which:
C is a constant related to the surface area of catalyst and microstructure and thickness of electrode.
Therefore, the ratio between $S_{cata}$ and $V_{reactant}$ is equal to $$\frac{4}{d}C.$$

Assuming that the surface area of the catalyst as well as the microstructure and thickness for different electrode are similar (i.e., similar C), a smaller d will result in a larger ratio between $S_{cata}$ and $V_{reactant}$, which means more catalyst surface area for the specific volume of reactant. As such, a microtubular reactor can provide sufficient catalyst area for the F-T process, resulting in excellent hydrocarbon yield.

Figure 2:
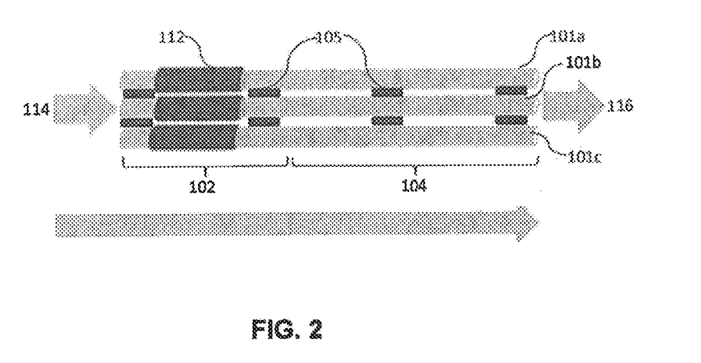
FIG. 2 illustrates a hydrocarbon generation system including a plurality of microtubular reactors.

A hydrocarbon generation system can include multiple microtubular reactors, each of which can include a first region that includes an SOEC and a second region within which an F-T reaction can be carried out. For example, in one embodiment multiple microtubular reactors can be combined to form a large hydrocarbon generation system, FIG. 2 illustrates an array that includes a plurality of individual microtubular reactors 101a, 101b, 101c, each of which including first region 102 that includes an SOEC 112 including a cathode, an anode, an electrolyte positioned between the cathode and anode, and a power source as discussed above. In addition, each of the microtubular reactors 101a, 101b, 101c include a second region 104 that includes an F-T catalyst downstream and in fluid communication with the cathode of the respective SOEC. During use, a $CO_2/H_2O$ feed 114 can be delivered to each microtubular reactor 101a, 101b, 101c, and the cathode reactions in the first regions 102 can form a syngas product including $H_2$ and CO that can flow to the second regions 104 that are at a lower temperature and contain the F-T catalyst for formation of hydrocarbons from the syngas as the flow passes through the reactor. The oxygen ion formed at each SOEC 112 can be transported across the electrolyte, either by diffusion alone or optionally in conjunction with an applied electrical gradient. The outflow 116 can include the hydrocarbons formed in the F-T reactions and the oxygen formed at the anode of the SOEC 112, generally in separate streams.

A system may include interconnections 105 that can separate each of the microtubular reactors from one another. The interconnections 105 may also serve to encase, or otherwise hold, the microtubular reactors in a desired array configuration. While the array of microtubular reactors illustrated in FIG. 2 includes only three microtubular reactors, it is understood that an array can include as many or as few microtubular reactors as desired. Furthermore, the microtubular reactors used to form an array can be configured in different positions within the array. For example, an array of microtubular reactors may include one or more microtubular reactors arranged in a planar fashion, such as being stacked in a horizontal or vertical configuration. Alternatively, the array may be configured in a circular fashion. Other array configurations may also be utilized according to embodiments of the invention and, as desired, multiple arrays may be associated.

A single feed stream 114 may feed H$_2$O and CO$_2$ (and optionally H$_2$) to each of the microtubular reactors in an array as illustrated in FIG. 2. In other embodiments, multiple feed streams (not shown) may feed H$_2$O and/or CO$_2$ and optionally H$_2$ to any combination of the microtubular reactors of an array. For instance, H$_2$O can be fed to some, or all, of the microtubular reactors in an array in conjunction with CO$_2$ in a single feed stream or in a separate feed stream, as desired. Various combinations of feed streams may be employed with embodiments of the invention to customize the component feeds to an array of microtubular reactors or to individual microtubular reactors.

The present disclosure may be better understood with reference to the Example, set forth below.

Example

Figure 3:
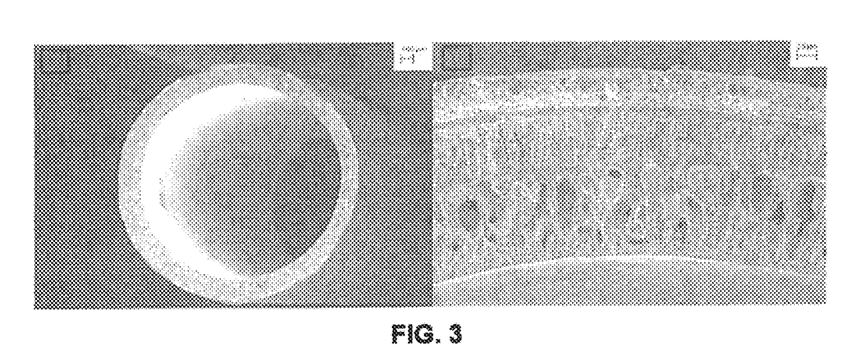
FIG. 3 includes low magnification (left) and high magnification (right) scanning electrode microscope (SEM) images of the electrolysis region of a microtubular reactor.

A microtubular SOEC was formed according to the methods described in U.S. Pat. No. 8,465,797 to Chen, et al., previously incorporated by reference. In FIG. 3 (left), a cross-sectional SEM image of the electrolysis region of the microtubular reactor is shown. The outer diameter of the electrolysis region was about 1.88 mm. It can be seen from the magnified image on the right of FIG. 3 that the electrolysis region contains three layers, namely: porous Ni—YSZ (8 mol % Y$_2$O$_3$-stabilized ZrO$_2$) cathode support, dense YSZ electrolyte film and porous LSM ((La$_{0.80}$Sr$_{0.20}$)$_{0.95}$MnO$_{3x}$))—YSZ anode layer. The Ni—YSZ support shows sandwich-like microstructure, with finger-like macrovoids near the lumen and outer sides and less porous layer in the middle.

Figure 4:
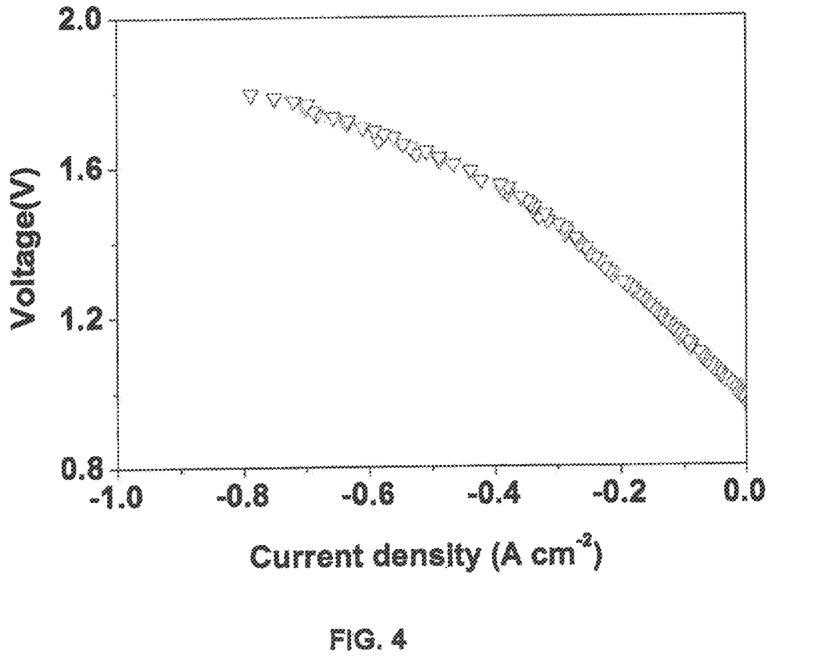
FIG. 4 presents a current/voltage (I-V) curve of an electrolysis process as described herein carried out at 750° C.

The electrochemical behavior of the electrolysis process was recorded, as shown in FIG. 4. The inlet gas flows were controlled to be 20 sccm, 5 sccm and 0.6 sccm for H$_2$, CO$_2$ and H$_2$O respectively. At 750° C., because of the reverse water-gas shift reaction, the gas component can vary. When the applied voltage was higher than the open circuit voltage (OCV), H$_2$O and CO$_2$ were electrochemically split to generate H$_2$ and CO. It can be seen that the current densities increased with the increase in the applied voltage. At 1.3 V, the current density was about $-0.24$ A cm$^{-2}$.

Figure 5:
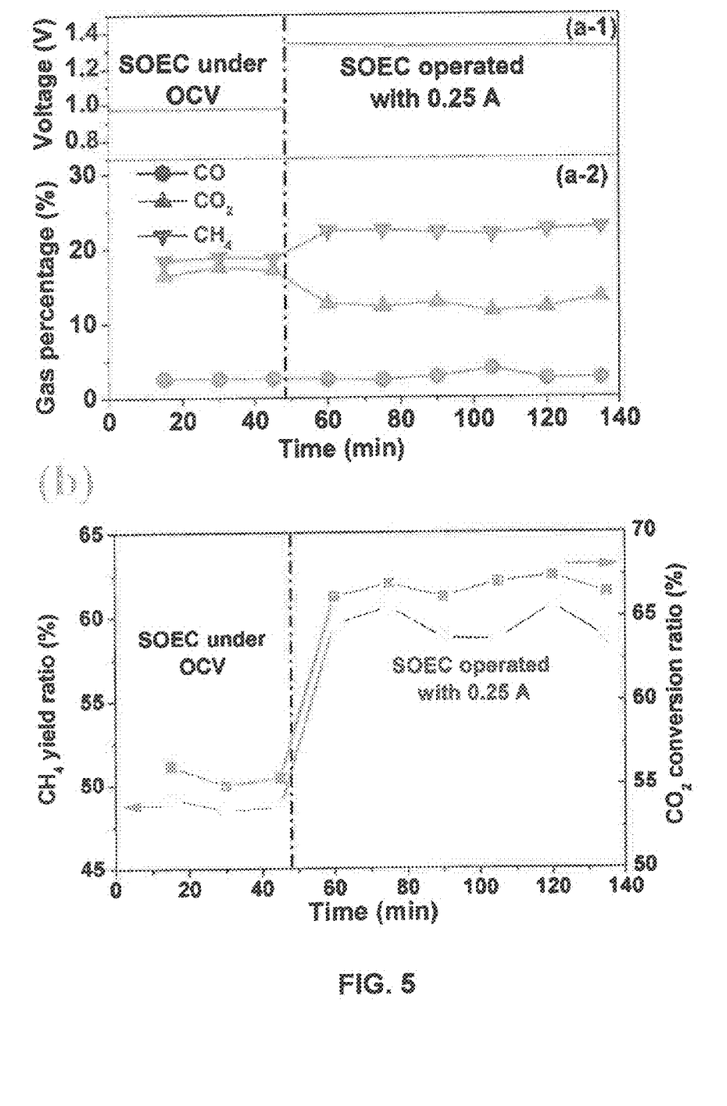
FIG. 5 graphically illustrates the effect of applied voltage on product gas component percentages in the exhaust (top; a-1 and a-2) and in $CH_4$ yield ratio and $CO_2$ conversion ratio (bottom; b) for a microtubular reactor as described.

As presented in FIG. 5 ($a$-1), the electrolysis region was first operated under OCV condition for an initial 48 min and then was operated with $-0.25$ A current. The exhaust gas was analyzed by GC and the result is shown in FIG. 5 ($a$-2). When the electrolysis region was operated under OCV condition, the feed gas flowed through the electrolysis region directly without any electrochemical reaction.

In the region of an F-T process, with the catalysis of Ni, which was located on the cathode on the inner wall of the microtubular reactor, H$_2$ reacted with CO or CO$_2$ to generate CH$_4$ through the conventional methanation process. From FIG. 5 ($a$-2), it can be seen that the percentage of CH$_4$ was about 18.5%, while the percentages of CO$_2$ and CO were approximately 16.9% and 2.6% respectively. Besides CH$_4$, CO$_2$ and CO, the remaining part of exhaust was mainly H$_2$, which is not shown in FIG. 5.

From FIG. 5 ($a$-1), it can be seen that when the electrolysis region is operated with $-0.25$ A current, the applied voltage remains stable at about 1.3 V. As seen in FIG. 5 ($a$-2), at a $-0.25$ A applied current, the proportion of CH$_4$ increased to about 22.3%, while the proportion of CO$_2$ decreased to about 12.8% and the proportion of CO remained stable at approximately 2.6%.

During the operation, the feed stream flowed through the electrolysis region where electrochemical splitting of H$_2$O and CO$_2$ and generation of H$_2$ and CO took place. According to Faraday's law, assuming 100% current efficiency, a current of $-0.25$ A consumed 1.74 sccm of H$_2$O and CO$_2$ and generated 1.74 sccm of H$_2$ and CO. Consequently, before entering the F-T reaction region, the gas will contain more H$_2$ and CO, compared with the electrolysis region under the OCV condition. For the methanation process in the F-T region, the increased H$_2$ or CO concentrations are kinetically favorable, and thus higher CH$_4$ yield is naturally achieved in the region of the F-T process.

According to the results illustrated in FIGS. 5 ($a$-1) and ($a$-2), the CH$_4$ yield ratio and CO$_2$ conversion ratio were calculated. The CH$_4$ yield ratio was calculated by equation (9):

$$\text{CH}_4 \text{ yield ratio} = [\text{CH}_4]/\{[\text{CH}_4] + [\text{CO}] + [\text{CO}_2]\} \quad (9)$$

and CO$_2$ conversion ratio was calculated by equation (10):

$$\text{CO}_2 \text{ conversion ratio} = \{[\text{CH}_4] + [\text{CO}]\}/\{[\text{CH}_4] + [\text{CO}] + [\text{CO}_2]\} \quad (10)$$

in which [X] is the volume percentage of gas. The calculated results are shown in FIG. 5 ($b$).

When the electrolysis region was operated under the OCV condition, the CH$_4$ yield and the CO$_2$ conversion ratio were about 48.7% and 55.5%, respectively. When the electrolysis region was operated with $-0.25$ A current, the CH$_4$ yield ratio and the CO$_2$ conversion ratio rose to about 59.3% and 66.9%, respectively.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A hydrocarbon generation system comprising:
   a plurality of microtubular reactors in an array, each microtubular reactor including
   a first region including a cathode and an anode in electrical communication with one another and an oxygen ion conducting electrolyte between the cathode and the anode,
   a second region including a Fischer-Tropsch reaction catalyst in fluid communication and downstream of the cathode; and
   a temperature control unit configured to provide the first region at a first temperature that is greater than a second temperature of the second region, wherein each microtubular reactor defines a continuous space, such that the first region and second region are in contact producing a temperature gradient along each microtubular reactor.

2. The hydrocarbon generation system of claim 1, wherein the outer diameter of the microtubular reactor is about 3 millimeters or less.

3. The hydrocarbon generation system of claim 1, wherein the cathode comprises nickel-yttria stabilized zirconia, nickel-samaria doped ceria, nickel-gadolinium doped ceria, perovskites having the general formula of La$_{1-x}$M1$_x$M2O$_{3-\delta}$ in which M1 is an alkaline earth element and M2 is a transition metal element, Sr$_2$Fe$_{2-x-y}$Mo$_x$M$_y$O$_{6-\delta}$ in which M is a transition metal element, and combinations there.

4. The hydrocarbon generation system of claim 1, wherein the anode comprises lanthanum strontium cobalt iron oxide, strontium-doped lanthanum manganite, strontium-doped lanthanum manganite impregnated with ceria-based catalyst, $Sr_2Fe_{2-x-y}Mo_xM_yO_{6-\delta}$ in which M is a transition metal element, $La_{1-x}M1_xM2O_{3-\delta}$ in which M1 is an alkaline earth element and M2 is a transition metal element, or combinations thereof.

5. The hydrocarbon generation system of claim 1, wherein the electrolyte comprises yttria stabilized zirconia, scandia stabilized zirconia, lanthanum gallate-based oxide, doped ceria, or combinations thereof.

6. The hydrocarbon generation system of claim 1, wherein the Fischer-Tropsch catalyst comprises cobalt, iron, nickel, nickel/platinum alloy, rhodium, ruthenium, palladium, osmium, vanadium, iron, manganese, or combinations thereof.

7. The hydrocarbon generation system of claim 1, wherein the cathode and the Fischer-Tropsch catalyst are on an inner surface of the microtubular reactor.

8. The hydrocarbon generation system of claim 1, wherein the cathode and the Fischer-Tropsch catalyst are on an outer surface of the microtubular reactor.

9. The hydrocarbon generation system of claim 1, wherein the cathode comprises the Fischer Tropsch catalyst.

10. The hydrocarbon generation system of claim 1, wherein the Fischer Tropsch catalyst comprises Ni and the hydrocarbon comprises methane.

11. The hydrocarbon generation system of claim 10, wherein methane comprises about 18% to about 23% of the hydrocarbon.

* * * * *